United States Patent [19]

Jimenez

[11] Patent Number: 5,423,773

[45] Date of Patent: Jun. 13, 1995

[54] CATHETER WITH GEAR BODY AND PROGRESSIVELY COMPLIANT TIP

[75] Inventor: Oscar Jimenez, Coral Gables, Fla.

[73] Assignee: Exonix Research Corp., Miami, Fla.

[21] Appl. No.: 184,489

[22] Filed: Jan. 21, 1994

[51] Int. Cl.⁶ .......................................... A61M 25/00
[52] U.S. Cl. ................................................ 604/282
[58] Field of Search ............... 604/282, 264, 280, 281, 604/273, 274, 96, 101; 606/191–194

[56] References Cited

U.S. PATENT DOCUMENTS

| | | | |
|---|---|---|---|
| 882,292 | 3/1908 | Brown . | |
| 3,314,449 | 4/1967 | Krone et al. | 138/125 |
| 3,498,286 | 3/1970 | Polanyi et al. . | |
| 3,684,605 | 8/1972 | Zwart | 604/282 |
| 3,860,040 | 1/1975 | Sullivan | 138/124 |
| 3,924,632 | 12/1975 | Cook | 604/282 |
| 4,261,390 | 4/1981 | Belofsky | 138/125 |
| 4,402,684 | 9/1983 | Jessup | 604/282 |
| 4,430,083 | 2/1984 | Gonz et al. | 604/283 |
| 4,547,193 | 10/1985 | Rydell | 604/282 |
| 4,840,623 | 6/1989 | Quackenbush | 604/280 |
| 5,069,674 | 12/1991 | Fearnot et al. | 604/282 |
| 5,176,126 | 1/1993 | Chikama | 604/282 |
| 5,275,152 | 1/1994 | Krauter et al. | 604/282 |

FOREIGN PATENT DOCUMENTS

| | | | |
|---|---|---|---|
| 0421650 | 4/1991 | European Pat. Off. | 604/282 |
| 2918282 | 11/1980 | Germany | 604/282 |

*Primary Examiner*—C. Fred Rosenbaum
*Assistant Examiner*—Manuel Mendez
*Attorney, Agent, or Firm*—Cesarano & Kain

[57] ABSTRACT

The present invention relates to an improved intravascular catheter. One improvement relates to the catheter body wherein the body is made of an inner tube of high temperature thermoplastic having a low coefficient of friction (for example fluorinated polymer). The extruded inner tube carries on its periphery a plurality of gear bodies. Each gear body further includes opposing elongated tangentially extending gear teeth spaced above the periphery of the tube. Wires are wound about the tube and over the gear teeth. An overcoat of low temperature thermoplastic covers the entire catheter and is interstitially disposed beneath the tangential teeth and the gear supported portions of the wire.

The overcoat of low temperature thermoplastic over the high temperature fluorinated polymer produces an interlocking gear thereby enhancing the lamination of both low and high temperature polymers. This coupled gear design makes possible a mechanical anchoring to fluorinated polymers such as TEFLON ® which are difficult, if not impossible, to bond.

Another improvement of the intravascular catheter involves the use of a progressively compliant tip at the distal end of the catheter body. This progressively compliant tip utilizes an endmost tubular member having a first softness and an intermediate tubular member having a second softness. The low temperature thermoplastic overcoat on the catheter body has a third softness which is significantly lower than the first and second degrees of softness exhibited by the other tubular members. The endmost member, intermediate member and thermoplastic overcoat are joined together by heat formed, blended tubular regions, each having respective incrementally increasing intermediate softness characteristics over predetermined lengths thereof. The incrementally increasing intermediate softness characteristic of these blended regions is formed by heated diffusion of the endmost member with the intermediate member, and further by the heated diffusion of the intermediate tubular member with the polymer overcoat. Accordingly, the softness and hence the compliancy of the distal end region of the catheter tip changes from the distal end of the tip (very soft) to the first blended tubular region (high-medium degree of softness), to the intermediate tubular member (medium degree of softness), to the further blended tubular region (medium-low degree of softness), and ultimately to the thermoplastic overcoat (low degree of softness).

22 Claims, 5 Drawing Sheets

CATHETER WITH GEAR BODY AND PROGRESSIVELY COMPLIANT TIP

The present invention relates to an intravascular catheter which can be used as an interventional guiding catheter, a coronary catheter, a radiology catheter or a neurology catheter. One improvement to the intravascular catheter includes a gear shaped catheter body and mechanically anchored wire that is anchored to the polymer overcoat of the catheter. Another improvement for the intravascular catheter includes a progressively compliant distal catheter tip.

BACKGROUND OF THE INVENTION

The guiding catheter is used in conjunction with coronary medical procedures, radiological medical procedures and neurological medical procedures. The guiding catheter provides a channel or tube for the further positioning of, for example, an angioplasty balloon catheter. The guiding catheter is initially positioned with the use of a guide wire. The balloon catheter or guide wire is introduced into the lumen of the guiding catheter and, for coronary catheterization, is advanced from the arterial entrance site of the patient to the ostium or septum of the potentially obstructed coronary artery. The ostium is the mouth-like opening in a body organ which, in coronary catheterization, is the heart of the patient. The guiding catheter supports the angioplasty balloon catheter as it is moved into the coronary artery and across the target lesion. Additionally, the guiding catheter allows monitoring of the aortic or coronary ostial pressure as well as visualization of the vascular system proximate thereto with the use of contrast media injections and electronic monitorization of the resulting radioactive emissions.

The guiding catheter forms a significant part of a more complex angioplasty system. This angioplasty system may include further devices for diagnostic purposes as well as interventional purposes. An ideal guiding catheter design may include the following elements:

A. The catheter should advance through the vascular system smoothly and responsively and permit precise maneuvering by the physician. The catheter should exhibit axial rigidity and responsiveness to torque forces applied by the physician at the proximal end of the catheter.

B. The catheter, and particularly the catheter tip, should be able to be positioned in the desired coronary ostium in a stable manner and without causing mural trauma or ostial occlusion. Mural trauma occurs when the tip or body of the catheter adversely affects the wall of the vessel. Specifically, the catheter tip should have memory and should further exhibit an elongated soft tip region to the vascular system and ostium.

C. The catheter tip should remain firmly engaged and present a stable platform in the ostium during introduction of the guide wire and/or angioplasty balloon catheter. That is, the tip and adjacent catheter body end region should provide mechanical backup and support for the other interventional and diagnostic equipment introduced into the lumen and projected from the catheter tip into the bodily organ.

D. The catheter should not become deeply engaged in the coronary artery during advancement or withdrawal of the angioplasty balloon catheter. In other words, the catheter should have a stable shaft and may include a braided wire to enhance mechanical support about the catheter body.

E. The internal lumen of the catheter body should remain lubricious to minimize friction during movement of the angioplasty balloon catheter therethrough. For example, the inner body of the catheter may be made of fluorinated polymer.

F. The catheter should allow adequate monitoring of the coronary ostial pressure and distal anatomy. In other words, the catheter should have an inner diameter retention.

G. The outer diameter of the catheter should present the smallest possible French size (circumferential diameter) to minimize trauma and bleeding at the insertion site. In other words, the catheter body should be as small as possible.

OBJECTS OF THE INVENTION

It is an object of the present invention to provide an improved intravascular catheter.

It is a further object of the present invention to provide a catheter having an elongated inner tubular body which has an inner lumen with a high degree of lubricity.

It is another object of the present invention to provide an intravascular catheter wherein wires are wound on the catheter body and are raised above the periphery of the inner tubular body with a plurality of gear shaped bodies.

It is an additional object of the present invention to provide mechanical anchoring between the wound wire, the gear bodies (and hence the inner catheter tubular body) and the outer polymer overcoat of the catheter body.

It is another object of the present invention to provide a catheter with a gear body which exhibits axial rigidity and a high degree of responsiveness to torque forces applied at the proximal end of the catheter by the physician.

It is a further object of the present invention to provide a catheter with a gear shaped body which remains firmly engaged and provides a stable interventional and diagnostic platform when the catheter tip is placed in the coronary ostium.

It is another object of the present invention to provide a gear shaped body which can be manufactured in a very small French size, thereby minimizing trauma and bleeding at the insertion site.

It is an additional object of the present invention to provide an intravascular catheter having a progressively compliant tip.

It is a further object of the present invention to provide a catheter wherein the tip region includes several tubular members having distinct degrees of softness (Shore hardness values) wherein those tubular members are joined by blended tubular regions having incrementally increasing intermediate softness characteristics over respective predetermined lengths thereof.

It is another object of the present invention to provide a soft tip catheter which eliminates radical transitions between tubular members having different degrees of softness which is a result of butt welding of the members together.

It is an additional object of the present invention to provide a soft tip catheter which minimizes mural trauma and ostial occlusion.

It is a further object of the present invention to provide a soft tip catheter which firmly engages and provides a stable mechanical platform in the arterial ostium.

It is another object of the present invention to provide a soft tip catheter which permits adequate monitoring of the coronary ostial pressure and distal anatomy, that is, the tip maintains its internal diameter during diagnostic and interventional procedures.

It is an additional object of the present invention to provide an intravascular catheter with a gear shaped body and a progressively compliant tip.

SUMMARY OF THE INVENTION

The present invention relates to an improved intravascular catheter. One improvement relates to the catheter body wherein the body is made of an inner tube of high temperature thermoplastic having a low coefficient of friction (for example fluorinated polymer). The extruded inner tube carries on its periphery a plurality of gear bodies. Each gear body further includes opposing elongated tangentially extending gear teeth spaced above the periphery of the tube. Wires are wound about the tube and over the gear teeth. An overcoat of low temperature thermoplastic covers the entire catheter and is interstitially disposed beneath the tangential teeth and the gear supported portions of the wire.

The overcoat of low temperature thermoplastic over the high temperature fluorinated polymer produces an interlocking gear thereby enhancing the lamination of both low and high temperature polymers. This coupled gear design makes possible a mechanical anchoring to fluorinated polymers such as TEFLON® which are difficult, if not impossible, to bond.

Another improvement of the intravascular catheter involves the use of a progressively compliant tip at the distal end of the catheter body. This progressively compliant tip utilizes an endmost tubular member having a first softness and an intermediate tubular member having a second softness. The low temperature thermoplastic overcoat on the catheter body has a third softness which is significantly lower than the first and second degrees of softness exhibited by the other tubular members. The endmost member, intermediate member and thermoplastic overcoat are joined together by heat formed, blended tubular regions, each having respective incrementally increasing intermediate softness characteristics over predetermined lengths thereof. The incrementally increasing intermediate softness characteristic of these blended regions is formed by heated diffusion of the endmost member with the intermediate member, and further by the heated diffusion of the intermediate tubular member with the polymer overcoat. Accordingly, the softness and hence the compliancy of the distal end region of the catheter tip changes from the distal end of the tip (very soft) to the first blended tubular region (high-medium degree of softness), to the intermediate tubular member (medium degree of softness), to the further blended tubular region (medium-low degree of softness), and ultimately to the thermoplastic overcoat (low degree of softness).

BRIEF DESCRIPTION OF THE DRAWINGS

Further objects and advantages of the present invention can be found in the detailed description of the preferred embodiments when taken in conjunction with the accompanying drawings in which.

DETAILED DESCRIPTION OF THE PREFERRED EMBODIMENT

Figure 1:
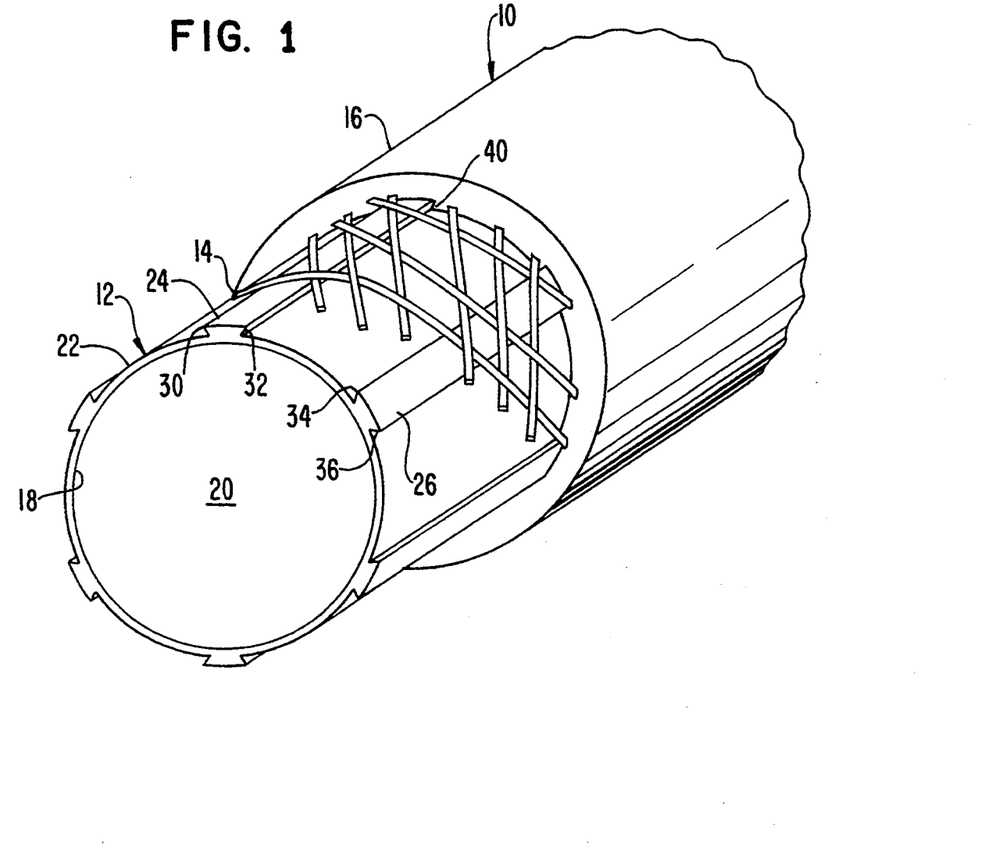
FIG. 1 diagrammatically illustrates a portion of a catheter body carrying gear shaped members, wound wires and an overcoat of thermoplastic thereon.
Figure 2:
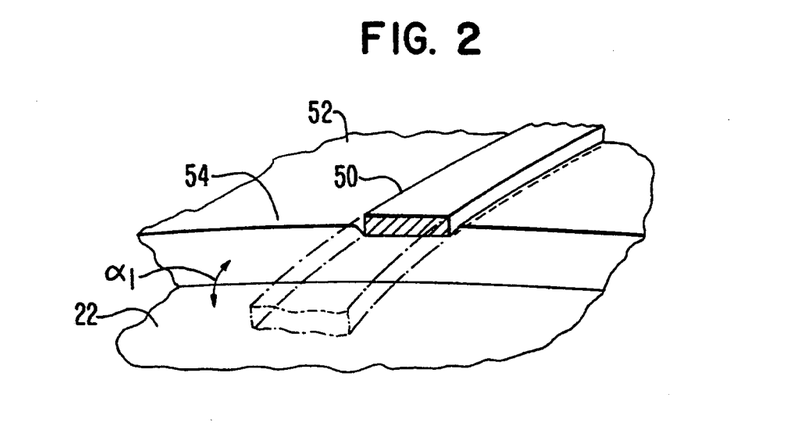
FIG. 2 diagrammatically illustrates one of the rectangular wires disposed over the gear body.
Figure 3:
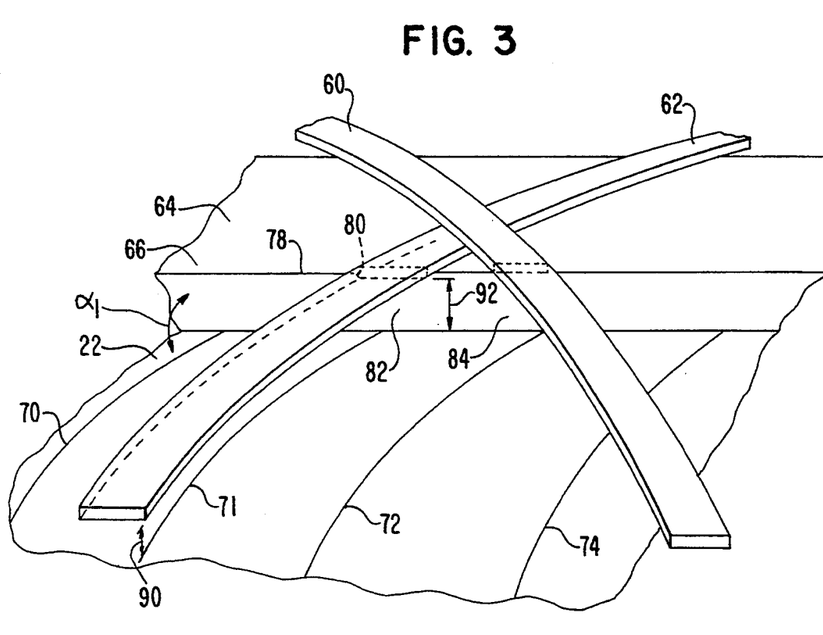
FIG. 3 diagrammatically illustrates a pair of crossed wires carried by a gear body.

The present invention relates to an intravascular catheter. One improvement involves the use of gear bodies placed on the extruded inner tube of the catheter body, wound wires over the top of these gear bodies and the disposition of the polymer overcoat of the gear body interstitially beneath the gear teeth and gear supported portions of the wire. Another improvement to the intravascular catheter involves the use of progressively compliant catheter tip. FIGS. 1–3 generally illustrate the gear body catheter and FIG. 9 diagrammatically illustrates the use of the gear body catheter. FIGS. 4–8 generally illustrate the catheter having a progressively compliant tip and FIG. 9 diagrammatically illustrates the use of such a catheter.

FIG. 1 diagrammatically illustrates an elongated catheter body 10 which includes an elongated inner tube 12, a plurality of wound wires, one of which is wire 14, and an overcoat 16 of low temperature thermoplastic. Preferably, elongated inner tube 12 is made of a high temperature thermoplastic having a low coefficient of friction. Specifically, tube 12 is an extruded tube of perfluorinated polymer, tetrafluoroethylene polymer (TFE) or polytetrafluoroethylene (PTFE). In one embodiment, inner tube 12 is made of TEFLON plastic. These perfluorinated polymers exhibit a very low coefficient of friction which provides a high degree of lubricity at inner surface 18 of lumen 20. The high degree of lubricity (or low coefficient of friction) enables catheter body 10 to easily carry and permit advancement (and retraction) of a guide wire or an angioplasty balloon catheter through its lumen. Of course, the perfluorinated polymer is a medical grade polymer with a degree of bio-compatibility.

Inner tube 12 includes, about its periphery 22, a plurality of gear bodies, two of which are identified as gear bodies 24 and 26. These gear bodies extend radially from periphery 22. Each gear body has opposing elongated tangentially extending gear teeth which are spaced above peripheral surface 22 of inner tube 12. In the illustrated embodiment, these tangentially extending gear teeth 30, 32 for gear body 24 and teeth 34, 36 for gear body 26, are formed during the extrusion of inner tube 12. In the illustrated embodiment and in a working embodiment, gear body 24 and teeth 30, 32 are generally shaped as a truncated frusto conical shape. In other words, teeth 30, 32 have a solid triangular cross section with respect to a plane perpendicular to the axial centerline of inner tube 12. In this sense, gear body 24 has a rectangular cross section and teeth 30, 32 are solid triangular bodies hung from the sides of the gear body.

Gear teeth 30, 32 form opposing tangentially extending lips which extend above and are spaced away from periphery 22 of inner tube 12. Gear teeth 30, 32 are elongated in the sense that they extend axially along the elongated inner tube 12. One of the purposes of providing opposing tangentially extending lips along the gear bodies is to enable overcoat 16 to lock onto, in a mechanical sense, to the gear bodies. As shown in region 40, overcoat 16 is disposed beneath tangential tooth 32, thereby providing a mechanical lock or tongue and groove mechanical configuration between overcoat 16 and inner tube 12.

This mechanical interlock is important because perfluorinated polymer (preferably TEFLON polymer) does not adhere well to the low temperature thermoplastic overcoat. This low temperature thermoplastic overcoat can be various polymers including nylon or a polyurethane coextrusion. A significant number of catheters use the fluoro polymer as an inner lining for the catheter body. In the present invention, the TEFLON inner tube 12 is extruded over a silver plated copper mandrel. In order to increase the adhesive characteristic of the TEFLON tube 12, the exterior surface of the TEFLON is chemically etched with sodium naphthalene which promotes adhesion to the otherwise adhesive surface.

In order to enhance the axial rigidity and torque responsiveness of the catheter body, a plurality of metal wires (one of which is wire 14) are wound about inner tube 12 and particularly over the gear bodies (two of which are bodies 24 and 26). Most significantly, these wires are wound over the gear teeth (specifically gear teeth 30, 32, 34 and 36). In a preferred embodiment, the wire is a stainless flat ribbon wire having a rectangular cross sectional shape. Also in a preferred embodiment, the wire is braided on tube 12 having the gear shaped bodies. In one embodiment, a 16 pick per inch braid is utilized. However, the braiding can be 20-32 picks per inch. Specifically, the stainless steel wire ribbon is grade SS 304 V spring tempered wire.

FIG. 2 diagrammatically illustrates wire 50 supported by a gear body 52 and passing over gear tooth 54. In the preferred embodiment, gear tooth 54 is angularly disposed at an acute angle such that angle $\alpha_1$ is less than 90° and preferably is approximately 60° from the tangential line extending from periphery 22 of the TEFLON inner tube. FIG. 2 diagrammatically illustrates wire 50 compressing gear tooth 54 as well as compressing the top surface of gear body 52. This compression of the gear tooth by wire 50 as it runs over the tooth further enhances the axial rigidity and the torque responsiveness of the body because the wire bites into gear body 52. This biting into the tangentially extending gear teeth provides a further mechanical lock between the inner tube carrying the gear bodies, the wire braiding, and the thermoplastic overcoat.

FIG. 3 diagrammatically illustrates a crossed pair of wires 60, 62 laid atop gear body 64. Gear body 64 includes gear tooth 66 that tangentially extends from the gear body over peripheral surface 22 of the TEFLON inner tube. In order to illustrate this spacing between the wire and the surface, peripheral surface 22 is illustrated with imaginary surface lines 70, 71, 72, and 74. In the preferred embodiment gear tooth 66 is angularly displaced with respect to peripheral surface 22 at angle $\alpha_1$, that is, approximately 60°. The bite of wire 62 on tooth edge 78 is shown by the dashed depression lines 80.

In order to provide an additional mechanical anchor or interlock between thermoplastic overcoat 10 and the adhesive surface 22 of TEFLON inner tube 12, the thermoplastic overcoat 16 is forced into the interspaces or interstices 82 and 84 beneath wires 60 and 62.

Further, wires 60 and 62 travel generally above surface 22 as noted by the decreasing and yet spatial displacement of the wires above surface 22 in FIG. 3. Compare distance 90 with distance 92. Of course, the gear bodies can be configured such that the wires touch peripheral surface 22 in the intermediary spaces between the gears. However, in a preferred embodiment, the wires stand above periphery 22 in these intermediary spaces. This causes substantially complete encapsulation of the wire above the adhesive surface 22.

There are six gear bodies equally spaced on the periphery 22 of the TEFLON or TFE inner tube in the preferred embodiment. FIG. 1 diagrammatically illustrates the preferred embodiment. Table 1 below provides exemplary dimensions for the gear body catheter. The hardness and conversely the softness of overcoat 16 is provided on the D scale in Durometers for Shore hardness factors.

TABLE 1

| Exemplary Dimensions for Catheter | | | |
|---|---|---|---|
| Gear | h | 0.0025 in. | |
| | w | 0.010 in. | |
| Position | α | 60° | |
| Tooth | α | 0.015R | |
| Body | I.D. | 0.070 in. | |
| | Wall | 0.002 in. | |
| Overcoat | O.D. | 0.087 in. | 55-75 D |
| Wire | h/w | 0.0010/0.003 in. | 16 pick/in. |

When the wire braid is positioned by the gear bodies above periphery 22, a floating wire construction is created. This may be conceptualized as mesh floating wires and permits substantially full metal encapsulation of the wire mesh by overcoat 16. This feature further improves the fluorinated polymer adhesion as well as provides kink resistance to the body of the catheter.

Overcoat 16 is, in a working embodiment, a radiopaque nylon or polymer having a 90D Shore hardness. This polymer overcoat is bio-compatible and provides additional axial rigidity, memory and diametric retention to the extruded inner tube 12.

The gear body and associated teeth can further be characterized as a wedge or a table top with opposing tangentially extending lips. Other modifications can be made such that the tangentially extending gear teeth need not run the entire length of the TEFLON inner tube. In other words, the tangentially extending gear teeth could be elongated and yet occupy distinct axial lengths along the catheter body.

Figure 4A:
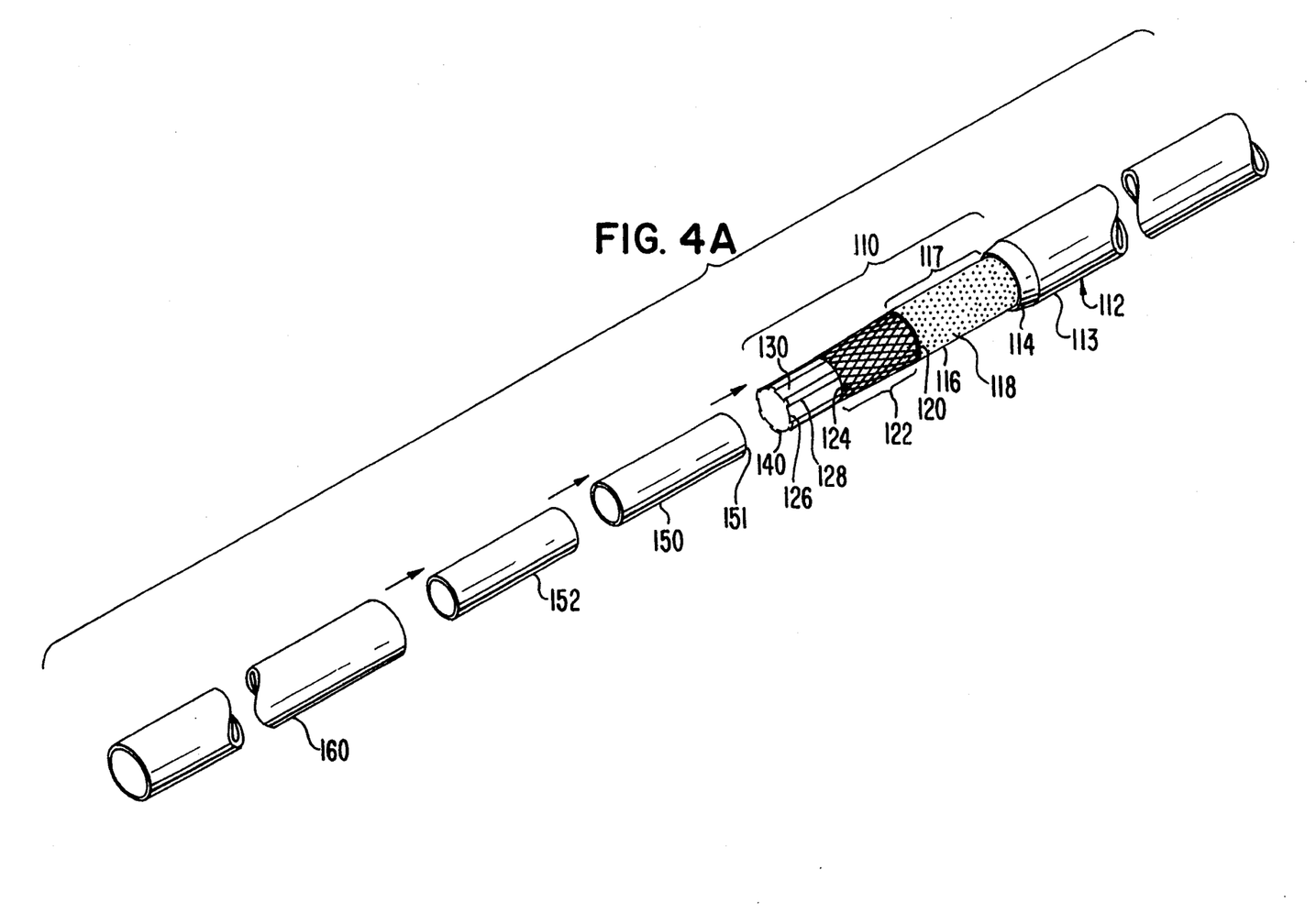
FIG. 4A diagrammatically illustrates an intravascular catheter having a progressively compliant tip and specifically the pre-assembly exploded view of that tip.
Figure 4B:
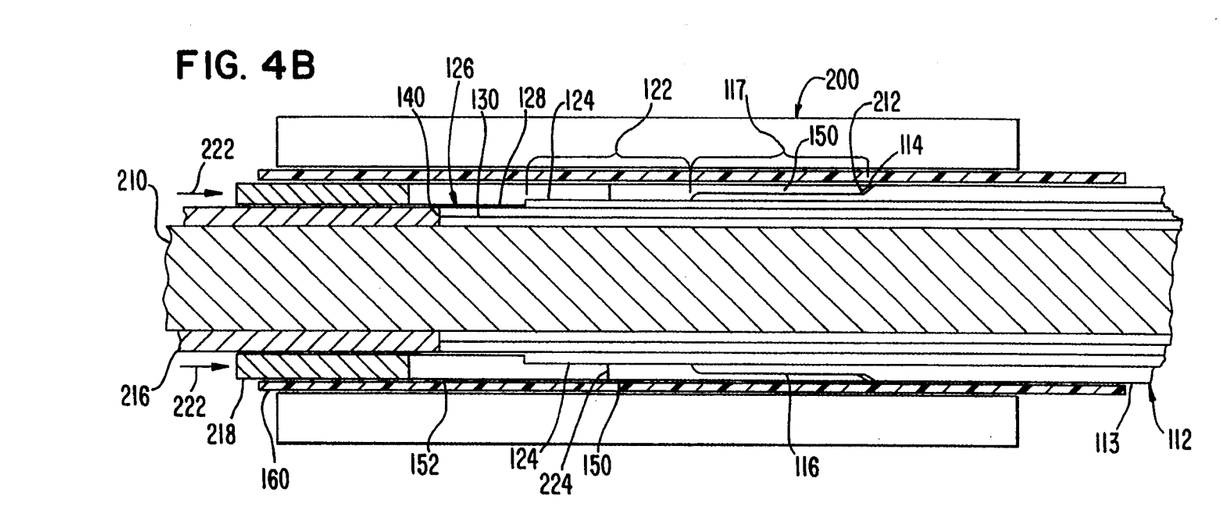
FIG. 4B diagrammatically illustrates the assembled tip region in a heated die.
Figure 5:
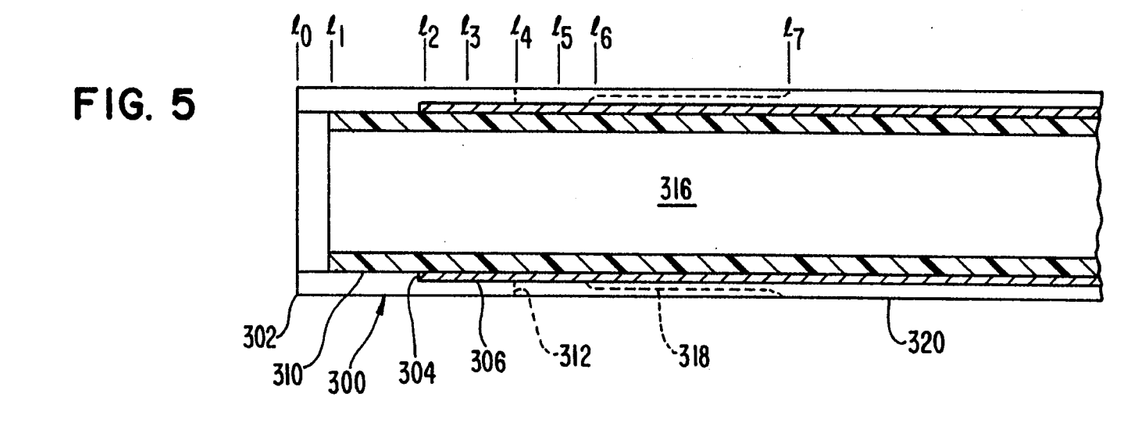
FIG. 5 diagrammatically illustrates the finished soft tip catheter and particular the tip region.
Figure 8:
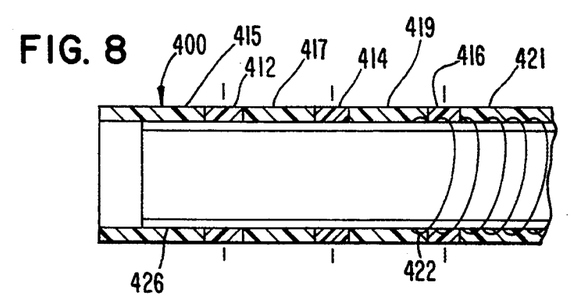
FIG. 8 diagrammatically illustrates the progressively compliant tip associated with another catheter body.
Figure 9:
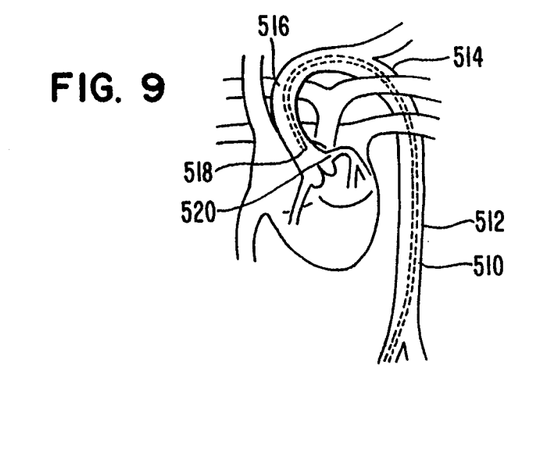
FIG. 9 diagrammatically illustrates the use of the intravascular catheter in a vascular system as a coronary guiding catheter.

FIGS. 4-8 diagrammatically illustrate the assembly, structural aspects of the progressively compliant tip for the improved intravascular catheter. FIG. 4A diagrammatically illustrates the preassembly of the progressively compliant tip catheter, FIG. 4B illustrates the tip in a heated die and FIGS. 5 and 8 diagrammatically illustrate the completed progressively compliant tip. FIG. 5 diagrammatically illustrates the compliant tip on a gear shaped body catheter, whereas FIG. 8 diagrammatically illustrates the compliant tip on another type of catheter body.

FIG. 4A diagrammatically illustrates the progressively compliant catheter tip in a preassembly stage. To create the progressively compliant tip, distal end region 110 is ground or cut from catheter body 112. Starting from catheter body 112, a primary slope 114 is established by grinding distal end 110 while the body is retained on a mandrel. In one embodiment, the primary slope is approximately 10° from the axial center line. The next distal most section 117 reveals uniformly distributed wire spot region 116 shown as dots in FIG. 4A (one of which is wire spot 118). The outer surface of section 117 is either level with or slightly below the top surface segments of the braided wire. A thin layer of the polymer overcoat is hence exposed over region 117. Polymer overcoat 113 has a softness characteristic generally within the range of 55-75 D Shore hardness. Distal end region 110 is further trimmed or ground with a secondary slope 120 which is approximately 0.5° in one embodiment. Proceeding towards end 140, wire braid 124 is fully exposed in bare wire braid region 122. At the terminal end of bare wire braid region 122, the inner tube 126 of the catheter body is exposed. In a preferred embodiment, inner tube 126 (preferably made of TEFLON polymer) includes a plurality of gear bodies, one of which is gear body 128. However, the progressively compliant soft tip catheter may utilize an inner tube 126 which does not include gear bodies protruding radially therefrom. In such a situation, inner tube 126 would provide a generally smooth, uniform peripheral surface similar to intermediate region 130 throughout its exposed axial length.

Two tubular sections, sleeves or members are forced into and over distal end region 110. An intermediate tubular section 150 has an intermediate softness characteristic within the range of 55-75 D Shore hardness. The end most tubular section 152 has the greatest softness characteristic in the range of 30-45 D Shore hardness. The combination of end most tubular section 152, intermediate section 150, and the low temperature thermal plastic overcoat 113 is further processed to develop a progressively compliant distal tip for intravascular catheter. In a preferred embodiment, the inner lumen wall at proximal end 151 of intermediate tubular section 150 is trimmed such that it overrides slope section 114. Further, TEFLON inner tube 126 is preferably chemically etched with sodium naphthalene before insertion of softer low temperature thermal plastic sleeves 150 and 152. After insertion of thermal plastic sleeves 150 and 152, a TEFLON tube 160 is placed over the entire assembly.

FIG. 4B diagrammatically illustrates the assembly step wherein the components for the progressively compliant catheter tip are placed into die 200. Similar numerals designate similar items in FIGS. 4A and 4B. Due to the complexity of the assembled structure, wire braid 124 is illustrated as a continuous layer in FIG. 4B. Similarly, gear body 128 is illustrated as a continuous layer protruding above periphery 130 of inner tube 126. Preferably, catheter body 112 is first placed on a mandrel 210. The distal end 110 (FIG. 4A) is grounded away. Thereafter, the catheter is placed on another mandrel or the same is used and soft sleeves 152, 150 are placed over the distal end region 110. As shown in FIG. 4B, the end most soft tubular sleeve 152 extends beyond distal end 140 of the ground down catheter body 112. Certain aspects of the physical structure are exaggerated in FIG. 4B. For example, the spot wire section 117 is greatly exaggerated such that the figure seems to indicate that intermediate tubular section 150 is greatly thinned. In fact, although the proximal inner end region 212 of intermediate tubular section 150 is trimmed, the bulk of the tubular section is forced over the proximal region of bare wire braid region 122 as well as all of spot wire region 117. Mandrel 210 may include a supplemental sleeve 216 in order to provide support for the distal end most portions of end sleeve 152.

An important aspect of the present invention involves the use of vent sleeve 218 which is axially movable with respect to mandrel 210. Particularly, catheter body 112 is gripped with an appropriate mechanical device on the right hand side of thermally controllable hot die 120. An axially directed force shown by arrows 222 forces vent sleeve 218 inboard which applies an axial pressure against both end most sleeve 152 and intermediate sleeve 150. This further enhances the pressure at fusion joint 224 and over the fusion region defined by spot wire segment 117. Die 120 is clamped about the end segment 110 of the catheter tip and heat in the range of 425°-475° F. (preferably 450°) is applied by the die to the tip. The application of heat occurs simultaneously with the axial force directed on vent sleeve 218 of the direction 222. TEFLON outer retainer 160 does not melt in this temperature range and serves to retain the tubular symmetry of the melted soft segment after removal from the hot die. TEFLON is also used in order to enhance the removability of the catheter tip from the die.

In order to color code the degrees of softness of these two sleeves in contrast to overcoat 113, the end most tubular 152 is orange and the intermediate sleeve 150 is green whereas the polymer overcoat 113 is white. Although intermediate tubular sleeve 150 can have a softness characteristic from 55-75 D Shore hardness, and polymer overcoat 113 can have a softness degree within approximately the same range (55-75 D), it is important that the intermediate polymer sleeve 150 have a softness characteristic intermediate the soft tip sleeve 152 and the significantly harder polymer overcoat 113.

Heat is applied for approximately 10 seconds by the die.

Figure 6:
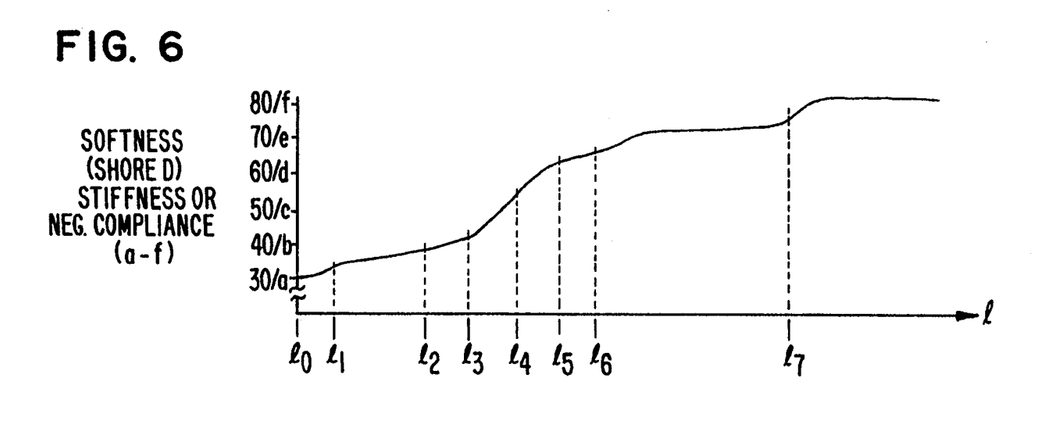
FIG. 6 diagrammatically and graphically illustrates the softness or compliant characteristic of the tip versus the length from the distal end of the tip.

FIG. 5 diagrammatically illustrates the progressively compliant soft tip 300 made in accordance with the principles of the present invention. Due to the difficultly involved in illustrating the complex compositional structure of the tip, reference will be made concurrently to FIG. 5, showing the progressively compliant distal end region tip 300, and FIG. 6 showing a graphic illustration of the softness versus length 1. Of course, increasingly larger numbers on the abscissa indicate lower degrees of softness, higher degrees of Shore hardness (D scale), lower degrees of compliance and higher degrees of stiffness. Beginning at distal end tip 302 at length $l_0$, the tip shows the highest degree of softness. This is equivalent to 35 D Shore hardness in one of the working embodiments. Of course, since only the end of the soft low temperature thermal plastic sleeve is presented between distance $l_0$ and $l_1$, this tip region exhibits the highest degree of compliance over that axial segment. Compliance, a general sense, reflects the amount of flexibility of the composite structure. To reduce mural trauma to the vascular system, the catheter tip must present not only a soft surface to the vascular walls but also a reasonable degree of compliance such that the catheter tip bends or flexes rather than tears through the vascular walls upon introduction and guiding of the catheter into the vascular system. Over length region $l_1$-$l_2$ immediately preceding distal end 304 of braid 306, the softness exhibited by catheter tip 300 is slightly lower than the initial softness or compliance at distal end 302 ($l_0$) due to the introduction of supporting inner tube structure 310. Negative compliance is graphically measured in FIG. 6 at levels a–f representing, in an illustrative fashion, increasingly stiffer structural elements which are less compliant than other elements closer to distal end 302. In the region between $l_{11}$-$l_2$, the compliance of distal tip 300 is reduced due to the presence of the underlying TEFLON tube 310. Beginning at distance $l_2$, wire braid 306 further enhances the stiffness of distal tip 300 represented as increasingly greater negative compliance.

Beginning at length $l_3$, through $l_4$ and until length $l_5$, the progressively compliant distal tip 300 defines a blended tubular region. The fusion plane or original physical contact between endmost soft sleeve 152 and intermediate soft sleeve 150 is shown as dashed line 312 at length $l_4$. However, since the two low temperature thermal plastic tubes have relatively the same melting point, polymer from the softer tube 152 flows into and mixes with polymer from tube 150 by heat diffusion. Polymer also is blended by the axial pressure and the radially directed pressure from die 200 into and through length $l_3$-$l_5$. The blended tubular region in segment $l_3$-$l_5$ exhibits incrementally increasing intermediate softness characteristic over the predetermined length $l_3$-$l_5$.

Figure 7:
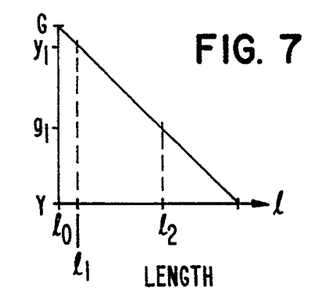
FIG. 7 graphically illustrates the color or compliance factor versus the length of the tip.

In an experiment, graphically illustrated in FIG. 7, two low temperature thermal plastic tubes were heat fused under axially and radially directed pressure. The softest tube was green and the harder tube was yellow. It has been visually confirmed that over a length $l_1$-$l_2$ (FIG. 7), there is a distinct and uniformly changing color variation from the pure green (length $l_0$-$l_1$) to the pure yellow (beyond length $l_2$) thermoplastic sleeves. Further, the compliance or softness of this composite structure varies in a some what linear fashion over the blended tubular end region $l_1$-$l_2$. In FIG. 7, $g_1$ indicates the first visual signs of green tint and level $y_1$ indicates the first visual signs of yellow tint.

Returning to FIGS. 5–6, the blended region $l_3$-$l_5$ exhibits incrementally increasing intermediate softness characteristics over the predetermined axial length of the tip. At length $l_5$, the softness is estimated to be about 60 D Shore hardness. In contrast, at the original joint between tubular sleeves 150, 152, (length $L_4$), a softness of approximately 50 D Shore hardness is exhibited. At length $l_3$, a Shore hardness of approximately 40 D Shore hardness is exhibited. Accordingly, the Shore hardness and conversely the softness of the incremental segment $l_3$-$l_5$ exhibits a somewhat linear transition for approximately 40 D through approximately 60 D.

This increasingly intermediate softness characteristic is very different from butt welded tubular sleeves. When two tubular sleeves are butt welded together, it is inevitable that there is some heat diffusion between the two sleeves. However, the softness transition across the butt welded joint is quite radical and occupies an extremely small axial distance. With such a radical transition which occurs with butt welding, any reasonable force normal to the axial center line of the catheter may kink or collapse the circumference of the catheter. If the catheter collapses, the lumen of catheter closes, thereby inhibiting the flow of radiopaque media or significantly affecting the passage of radiopaque media or a balloon catheter therethrough. During utilization of the catheter, the vascular system continues to pump blood and other fluids therethrough. During insertion and while in a stationary position, the catheter is subjected to continuously variable physical forces acting. When the physician is attempting to torque or rotate the catheter or guide the catheter to a specific location within the vascular system, it is critically important that the catheter tip be as soft as reasonably possible present a relatively compliant tip region as well as provide reasonable support any interventional or diagnostic elements sled through its lumen 316. A butt welded joint may collapse during the medical procedure due to these variables forces acting on the catheter.

Beginning at axial distance $l_6$, a thin layer of overcoat 318 is found beneath the intermediate tubular sleeve. Since the heat applied by the die to the composite structure causes the polymers in the intermediate sleeve and the low temperature thermoplastic overcoat 320 to migrate and mix throughout length $l_6$-$l_7$. The compliance in the axial region $l_6$ and $l_7$ generally increases from approximately 60 D Shore hardness to approximately 75 D. Beyond distance $L_7$, overcoat 120 is presented to the vascular walls. Accordingly, if overcoat has a Shore hardness of approximately 75 D that aspect of the catheter is presented to the vascular system.

As can be seen by FIG. 5, the axial length of the blended region between $l_3$ and $l_5$ is generally equivalent to the length of the softest or end most tube between $l_0$-$l_3$. Further, the transitional period between the intermediate tube and the overcoat, that is, blended tubular region $l_6$-$l_7$ is very large as compared with the unaffected intermediate tubular soft section between $l_5$ and $l_6$.

FIG. 7 diagrammatically illustrates that with the use of color coded tubular sections and overcoats, the degree of softness, and hence the degree of compliance, can be visually displayed by the color blend along the axial sections of the tip. In one embodiment, the end most sleeve was 35 D, the intermediate sleeve was 90 D and the overcoat was 90 D. However, because of the underlying wire braid, an increasingly greater degree of compliance is established between the catheter body and the distal end of the tube. All three grades of plastic, the end most sleeve, intermediate sleeve and thermal plastic overcoat are designed to melt at temperature approximately below 300° C. or below approximately 500°–600° F. As is known, the TEFLON inner tube is not significantly affected at temperatures between the ambient and 500° F. (260° C.).

FIG. 8 diagrammatically illustrates another progressively soft tip catheter 400 having blended regions 412, 414 and 416 caused by heated diffusion of end most section 415 into first intermediate section 417 and heat diffusion of section 417 into section 419 and further the heat diffusion of section 419 into section 421. A wire braid 422 is diagrammatically illustrated as beginning slightly before the blended tubular region 416. Perfluorinated polymer inner tube 426 provides underlying support for tubular sections 415, 417, 419 and 421. The low temperature thermal plastic overcoat is not shown in conjunction with FIG. 8.

Experiments have been conducted which reveal that a progressively compliant catheter tip can be manufactured from four different tubular sleeves each having distinct softness characteristics. Further, blended softness regions have been created between each of these four sleeves. Accordingly, in order to obtain the progressively compliant distal end for the intravascular catheter, the desired number of low temperature thermal plastic sections can be assembled and placed under both axial compression as well as radial compression simultaneous with the application of heat. This causes the formation of blended tubular regions rather than radical transitions which occur with butt welding between these plastic sleeves.

The following table presents exemplary data for a soft tip catheter.

TABLE 2

| Exemplary Tip Data | | |
| --- | --- | --- |
| Soft Tip | 30–45 D (Shore) | orange |
| Intermediate Tip | 55–75 D | green |
| Poly Overcoat | 55–75 D | white |
| Primary Slope | α  10° | |
| Spot Wire length | 0.75 in. | |
| Secondary Slope | α  0.5° | |
| Bare Braid Wire length | 0.6 in. | |
| Exposed Gear length | 0.5 in. | |

FIG. 9 diagrammatically illustrates guiding catheter 510 being fed through vascular system 512. The catheter has been placed through the descending aorta 514 as well as into ascending aorta 560. Catheter end 518 is relatively close to the left coronary ostium 520.

The gear shaped guiding catheter described in conjunction with FIGS. 1–3 can be used in this manner.

The soft tip catheters shown in FIGS. 5 and 8 can also be used in a manner as shown in FIG. 9.

The claims appended hereto are meant to cover modifications and changes within the spirit and scope of the present invention.

What is claimed is:

1. An intravascular catheter comprising:
   an elongated inner tube made of a high temperature thermoplastic having a low coefficient of friction;
   a plurality of gear bodies radially extending from and spaced about the periphery of said inner tube, each gear having opposing, elongated, tangentially extending gear teeth above said periphery of said inner tube, said gear teeth defining opposing, elongated, tangentially extending lips from said gear body;
   a plurality of wires wound about said inner tube over said gear teeth; and
   an overcoat of low temperature thermoplastic, said overcoat covering the entire catheter and interstitially disposed beneath said tangential teeth and gear supported portions of said wire.

2. A catheter as claimed in claim 1 wherein said inner tube is made of tetrafluoroethylene polymer and said wires are metal and bite into said tangentially extending teeth.

3. A catheter as claimed in claim 1 wherein said wires and metal and said inner tube is made of perfluorinated polymer which establishes an inner lumen with a high degree of lubricity.

4. A catheter as claimed in claim 1 wherein said gear teeth have a triangular cross-section.

5. A catheter as claimed in claim 4 wherein said wire has a rectangular cross-sectional shape.

6. A catheter as claimed in claim 5 wherein said wire is braided on said inner tube.

7. A catheter as claimed in claim 6 wherein said wire causes localized compressed and depressed regions on a top surface of said gear teeth.

8. A catheter as claimed in claim 7 wherein said wire is spaced above the periphery of said inner tube in intermediary spaces between gears.

9. A catheter as claimed in claim 8 wherein six equally spaced apart gears are disposed on the periphery of said inner tube.

10. A catheter as claimed in claim 1 wherein said wire has a rectangular crosssectional shape.

11. A catheter as claimed in claim 10 wherein said wire is braided on said inner tube.

12. A catheter as claimed in claim 1 wherein said wire causes localized compressed and depressed regions on a top surface of said gear teeth.

13. A catheter as claimed in claim 12 wherein said wire is spaced above the periphery of said inner tube in intermediary spaces between gears.

14. A catheter as claimed in claim 1 including a progressively compliant distal end region.

15. A catheter as claimed in claim 18 wherein said overcoat having a first softness characteristic, said catheter having a distal end region defined by:
   an endmost, low temperature, thermoplastic tubular section having a second softness characteristic that is significantly greater than said first softness;
   another low temperature, thermoplastic tubular section having a third softness characteristic that is medium with respect to said first and second softness, said other tubular section disposed between said endmost section and said overcoat; and,
   blended tubular regions formed by heated diffusion of said endmost section with said other section and said other section with said overcoat, each said blended region having respective incrementally increasing intermediate softness characteristics over predetermined lengths thereof.

16. A catheter as claimed in claim 15 wherein the outer dimension of said endmost and said other section is substantially equivalent to an outer dimension of said overcoat.

17. A catheter as claimed in claim 15 wherein said low temperature thermoplastic overcoat, said low temperature thermoplastic endmost section, and said low temperature thermoplastic other section all melt at temperatures below approximately 300 degrees Centigrade.

18. A catheter as claimed in claim 15 wherein said first softness is within the range of 55–75 D Shore hardness, said second softness is within the range of 30–45 D Shore hardness, and said third softness is less than said first softness and within the range of 55–75 D Shore hardness.

19. A catheter as claimed in claim 18 wherein said endmost section, said other section and said overcoat are color coded, each with a distinct color.

20. A catheter as claimed in claim 19 wherein said blended regions exhibit a color blend generally indicative of said incrementally increasing softness characteristic.

21. A catheter as claimed in claim 20 wherein the blended region between said other section and said overcoat contains incrementally greater amounts of said overcoat dependent upon the distance to said distal end of said catheter.

22. A catheter as claimed in claim 1 wherein six equally spaced apart gears are disposed on the periphery of said inner tube.

* * * * *